(12) United States Patent
Barres et al.

(10) Patent No.: US 6,515,738 B1
(45) Date of Patent: Feb. 4, 2003

(54) METHOD OF DETERMINING THE AUTHENTICITY AND THE GEOGRAPHICAL ORIGIN OF GEMSTONES SUCH AS BERYLS

(75) Inventors: Odile Barres, Richardmenil (FR); Bruno Sabot, Nancy (FR); Alain Cheilletz, Nancy (FR); Philippe de Donato, Varangeville (FR)

(73) Assignee: Mauboussin Successeur de Noury, Paris (FR)

( * ) Notice: Subject to any disclaimer, the term of this patent is extended or adjusted under 35 U.S.C. 154(b) by 5 days.

(21) Appl. No.: 09/618,134

(22) Filed: Jul. 17, 2000

(30) Foreign Application Priority Data

Jul. 15, 1999 (FR) .............................. 99 09175
Dec. 20, 1999 (FR) .............................. 99 16057

(51) Int. Cl.⁷ .............................. G01N 21/87
(52) U.S. Cl. .............................. 356/30
(58) Field of Search .............................. 356/30

(56) References Cited

U.S. PATENT DOCUMENTS

| 4,345,840 A |   | 8/1982 | Goetz et al. |        |
|-------------|---|--------|--------------|--------|
| 4,394,580 A | * | 7/1983 | Gielisse     | 356/30 |
| 4,534,644 A | * | 8/1985 | Beesley      | 356/30 |
| 5,536,943 A | * | 7/1996 | Smith et al. | 356/30 |

FOREIGN PATENT DOCUMENTS

| DE | 25 44 417  | 5/1976 |
| DE | 195 06 192 | 7/1995 |
| DE | 44 06 768  | 9/1995 |
| DE | 196 10 393 | 9/1997 |
| EP | 0 071 462  | 2/1983 |
| FR | 2 496 888  | 6/1982 |

OTHER PUBLICATIONS

D.L. Wood et al., *Infrared Spectra of Foreign Molecules in Beryl*, The Journal of Chemical Physics, vol. 47, No. 7, Oct. 1, 1967, p. 2220–2228.
J.E. Shigley, *The gemological identification of emeralds and blue sapphires*, CIM Bulletin, vol. 91, No. 1025, Nov./Dec. 1998, p. 91–96.
John I. Kolvula et al., *Gemological Investigation of a New Type of Russian Hydrothermal Synthetic Emerald*, Gems & Gemology, Spring 1996, p 32–39.
Karl Schmetzer et al., *Emeralds from the Ural Mountains, USSR*, Gems & Gemology Summer 1991, p. 86–99.

* cited by examiner

Primary Examiner—Richard A. Rosenberger
(74) Attorney, Agent, or Firm—Jacobson Holman PLLC

(57) ABSTRACT

The method of determining the authenticity and the geographical origin of gemstones of crystalline structure comprises the steps consisting in: applying an electromagnetic beam to the gemstone; determining values associated with the absorbance of the gemstone for wavelengths of the beam in an absorption direction that is predetermined relative to a characteristic axis of the crystal; calculating at least one ratio between these values; and comparing the or each ratio with predetermined corresponding ratios belonging to gemstones of predetermined authenticity and origin.

18 Claims, 4 Drawing Sheets

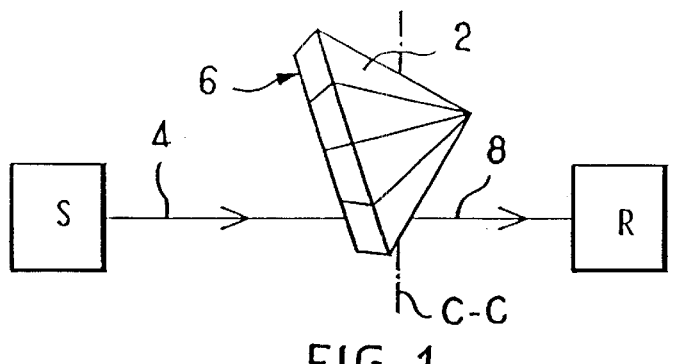
FIG_1
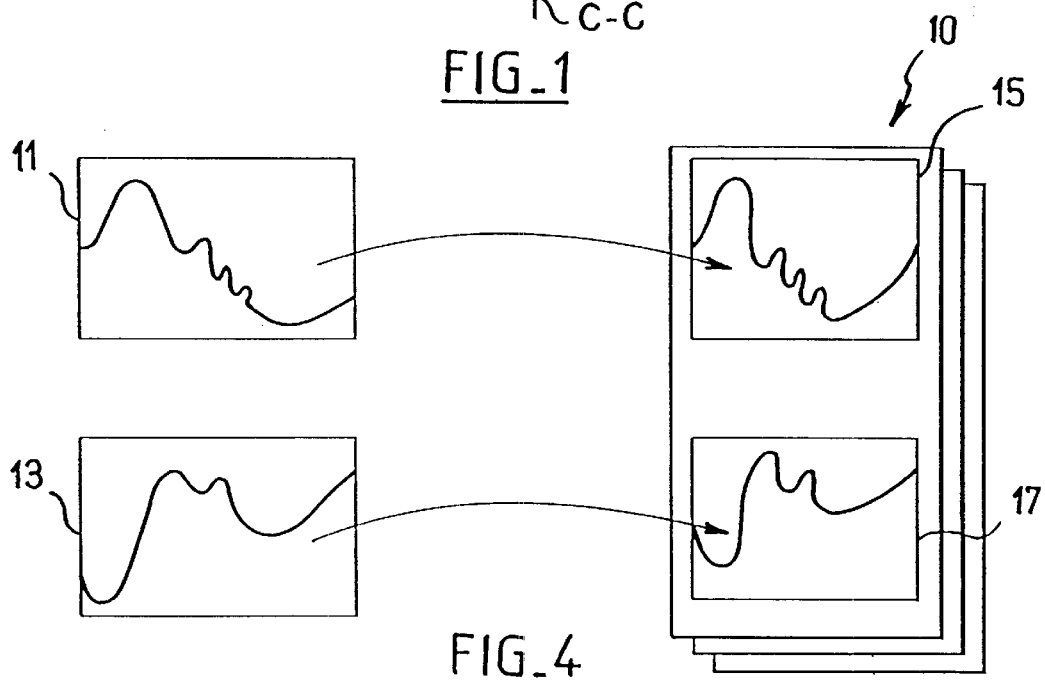
FIG_4
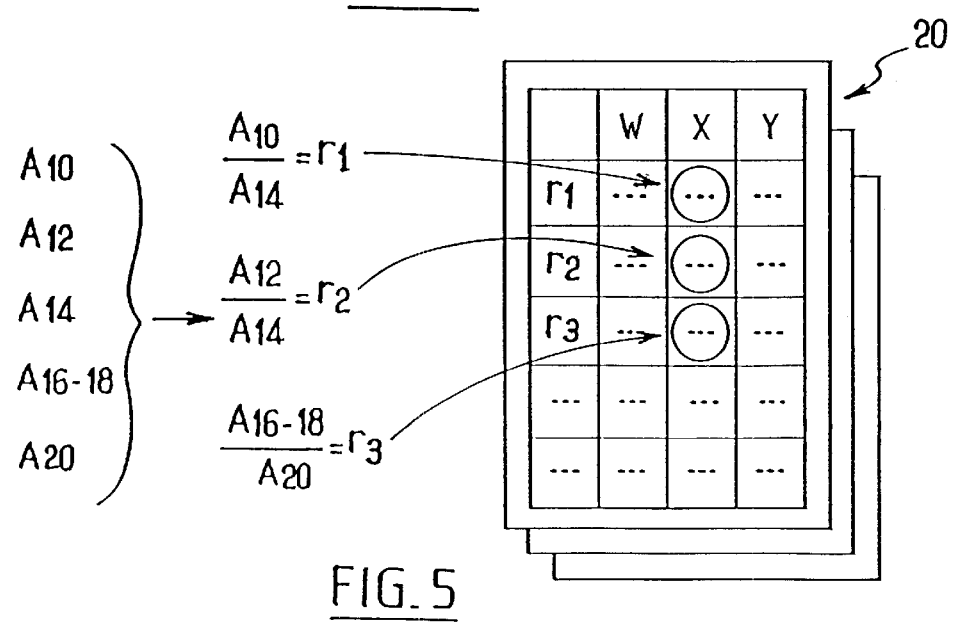
FIG_5

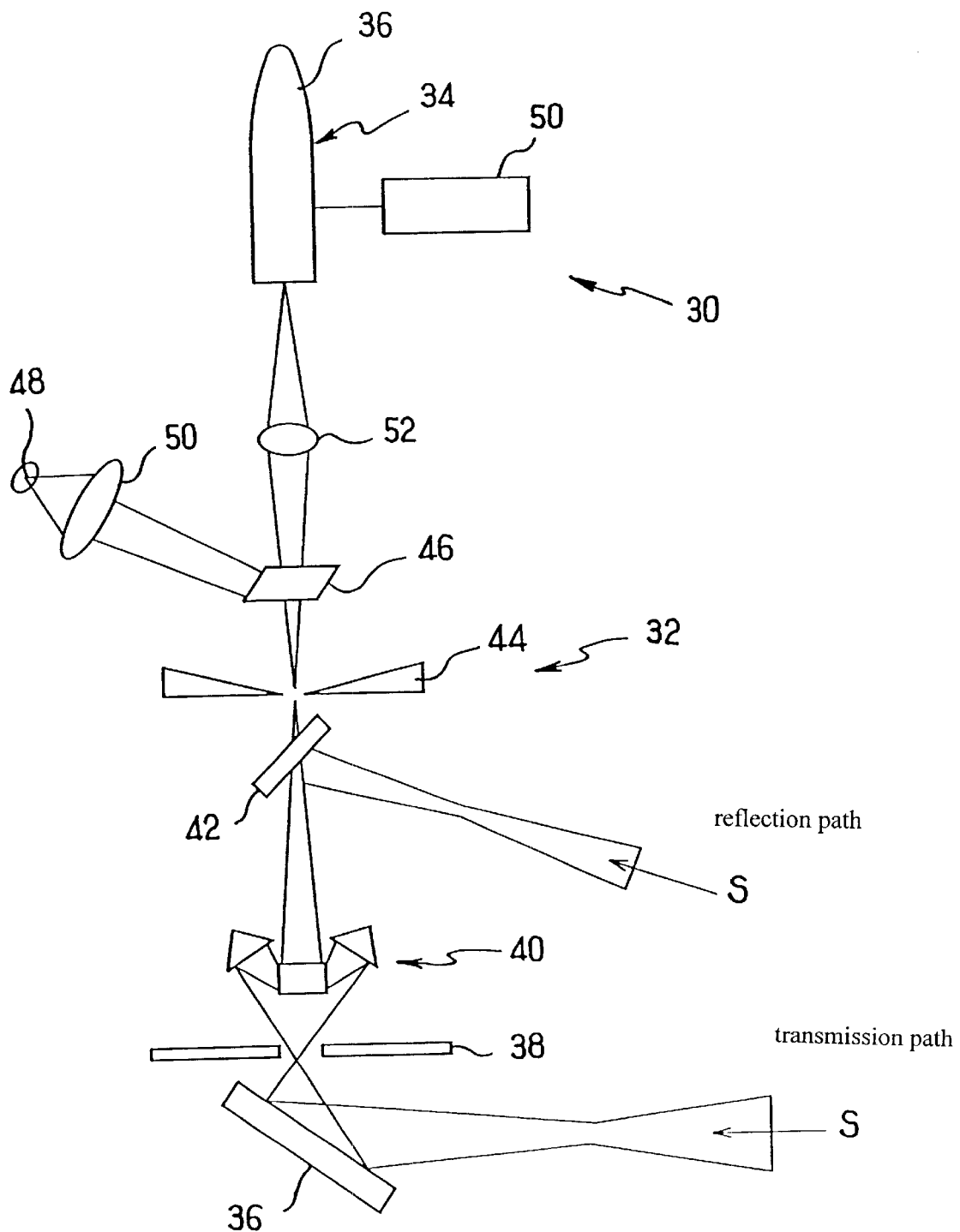
FIG_6

METHOD OF DETERMINING THE AUTHENTICITY AND THE GEOGRAPHICAL ORIGIN OF GEMSTONES SUCH AS BERYLS

The invention relates to determining the authenticity and the geographical origin of gemstones such as beryls and/or other silicates of similar crystallochemical structure.

BACKGROUND OF THE INVENTION

It has been known for a long time that gemstones can be the subject of more or less elaborate treatments to improve the appearance thereof, for example to make them more brilliant, or to modify said appearance, for example to change the color of the stone. There is a very wide variety of such treatments which include heating the stone, coloring it externally, or filling in its pores or cracks with polymers. Such treatments seek to pass off a stone of poor authenticity as a stone of better authenticity. There therefore now exists a strong demand for methods that enable the authenticity of a stone to be determined and that can detect any faking with a high degree of certainty. Such methods need to be of particularly high performance given that certain treatments of the stone are difficult to detect. Naturally, such methods must not be destructive and should not run the risk of modifying the physical characteristics of the stone. There also exists a demand for methods that make it possible to determine the exact geographical origin of a gemstone in terms of its original deposit.

A known method of determining whether a stone is natural or synthetic consists in performing infrared spectroscopy on the stone and comparing the general appearance of the resulting spectrum with the appearance of the spectrum from a stone of known kind in order to determine whether the stone under investigation is of the same kind. Nevertheless, that method is not sufficiently accurate and reliable so it is to be feared that it is unsuitable for revealing certain treatments of the stone.

OBJECTS AND SUMMARY OF THE INVENTION

An object of the invention is to provide a method making it possible to determine the nature of a gemstone or to detect any treatment it has received with greater accuracy, and even to determine the geographical origin of the stone.

According to the invention, this object is achieved by a method of determining the authenticity and the geographical origin of gemstones of crystal structure, the method comprising the steps consisting in: applying an electromagnetic beam to the gemstone; determining values associated with the absorbance of the gemstone for wavelengths of the beam in an absorption direction that is predetermined relative to a characteristic axis of the crystal; calculating at least one ratio between these values; and comparing the or each ratio with predetermined corresponding ratios belonging to gemstones of predetermined authenticity and origin.

Thus, by taking account of the orientation of the crystal when studying absorption it is possible to obtain measurements of very high accuracy, thus enabling the gemstone to be characterized in very reliable manner.

In addition, performing analysis by means of one or more ratios gives rise to quantitative results. This makes it possible to characterize a gemstone by one or more magnitudes that are independent of the dimensional characteristics of the stone under study, and that are a function solely of the crystallochemical composition of the stone. This quantitative data is suitable for being compared directly with corresponding magnitudes that are known for standard stones even if they are of dimensions that are very different from those of the stone under investigation. The accuracy and the reliability of the magnitudes used for comparison make it possible to detect a very wide variety of treatments that can be applied to a stone and/or, in the absence or in the presence of such treatment, to establish with a very high degree of probability the geographical origin of the stone in terms of country or indeed of deposit.

Advantageously, the values are absorbance intensities.

Under some circumstances, it can thus suffice to measure absorbance at given wavelengths, e.g. when it is necessary merely to validate the assumed nature and origin of a stone.

Advantageously, an absorption spectrum is established corresponding to the predetermined absorption direction.

This spectrum makes it possible in particular to perform initial qualitative analysis relating to general appearance so as to preselect a certain number of likely natures and geographical origins for a stone.

Advantageously, the values are areas defined by the absorption spectrum.

Performing calculations on the basis of suitably chosen areas gives results that are more accurate than when using intensities since the results are based on the integrals of measurements and not on the measurements themselves.

Advantageously, a beam is delivered along the predetermined absorption direction.

Advantageously, a plurality of beams are applied to the gemstone along different directions, values are determined associated with absorbance in the respective directions of the beams, and the values corresponding to the predetermined absorbance direction are calculated.

This variant makes it possible to eliminate random effects that are sometimes encountered when directing the beam in the predetermined absorption direction. With this direction being known, it suffices to perform measurements for the three beams that form the three respective axes, and then to combine the results, e.g. in linear manner, so as to reconstitute the corresponding values lying on the predetermined absorption direction. This enables these values to be obtained indirectly.

Advantageously, the predetermined direction is perpendicular to the c—c axis of the crystal.

This direction significantly amplifies the absorption characteristic of the mineral, and this direction makes it possible to obtain experimental data that is particularly characteristic of the composition of the mineral.

Advantageously, at least one of the wavelengths is such that the associated value characterizes the presence of a specific body.

Advantageously, at least one of the wavelengths is such that the associated value characterizes the presence of a specific isotope of a specific body.

Advantageously, at least one of the wavelengths is such that the associated value characterizes the presence of a specific isotope of a specific body, said isotope being in a specific configuration relative to the crystal.

The above two variants make it possible with good accuracy to determine the geographical origin of stones or to detect any possible treatment thereof.

Advantageously, the wavelengths are situated in the infrared range.

Advantageously, the absorbance values are determined from the beam coming from the gemstone after said beam has passed through a diaphragm and/or an objective lens.

Advantageously, the gemstone is a beryl or a cordierite.

The invention also provides apparatus for determining the authenticity and the geographical origin of gemstones of crystal structure, the apparatus comprising a source of an electromagnetic beam; means for determining values associated with the absorbance of the gemstone for wavelengths of the beam in an absorbance direction that is predetermined relative to a characteristic axis of the crystal; and calculation means for calculating at least one ratio between the values.

Advantageously, the apparatus includes means for comparing the or each ratio with corresponding predetermined ratios belonging to gemstones of predetermined authenticity and origin.

Advantageously, the apparatus includes means for causing the beam that comes from the gemstone to pass through a diaphragm and/or an objective lens.

BRIEF DESCRIPTION OF THE DRAWINGS

Other characteristics and advantages of the invention will appear more clearly on reading the following description of a preferred embodiment given by way of non-limiting example. In the accompanying drawings:

FIG. 1 is a block diagram of measurement apparatus for implementing the method of the invention;

FIGS. 4 and 5 show the respective steps of qualitative and of quantitative analysis in the method; and FIG. 6 shows a preferred embodiment of apparatus of the invention for implementing the invention.

MORE DETAILED DESCRIPTION

Figure 2:
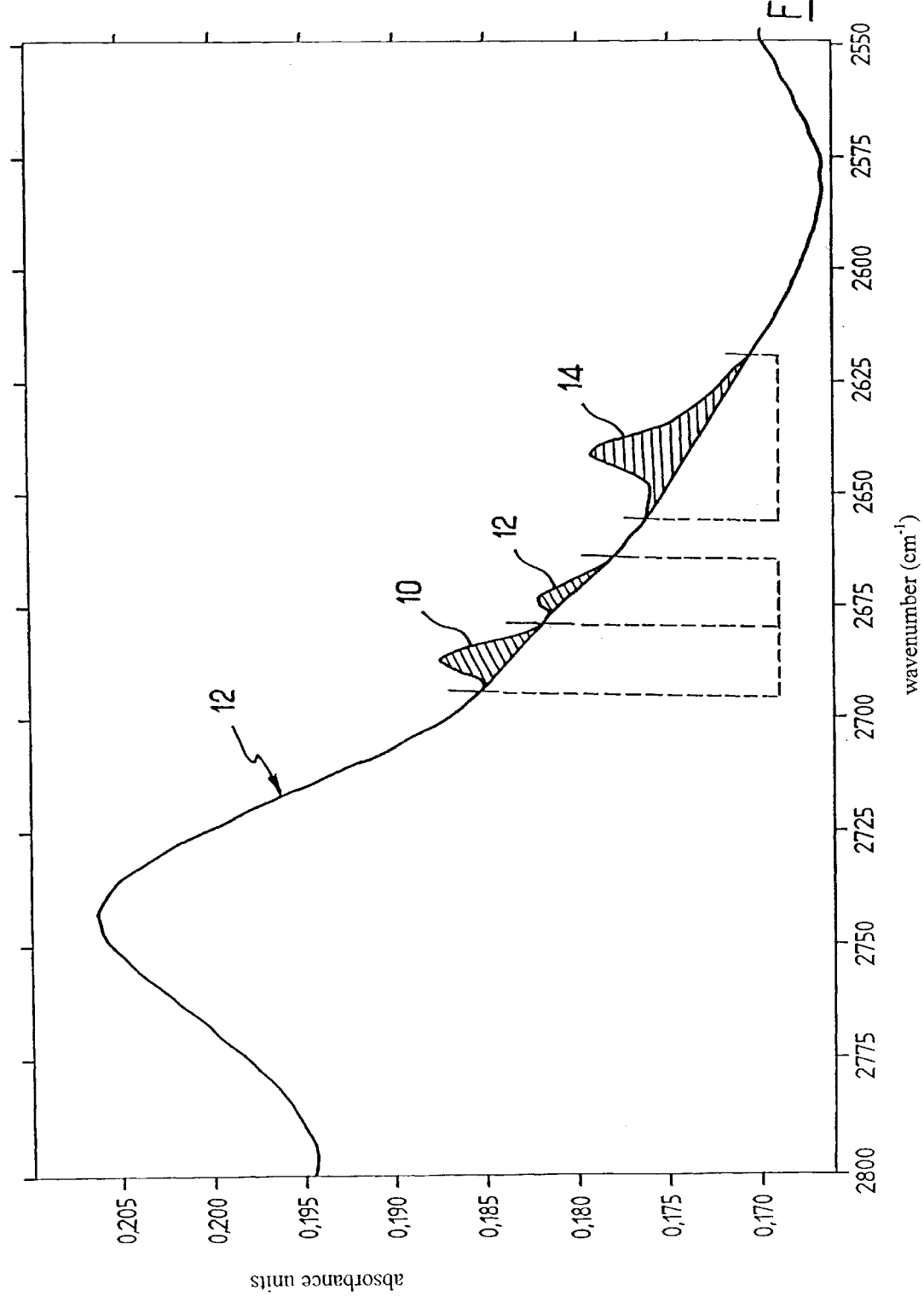
FIGS. 2 and 3 are two absorption spectra obtained by using the measurement apparatus of FIG. 1.

A preferred implementation of the method of the invention is described below with reference to FIGS. 1 to 5 for the purpose of determining the nature and the geographical origin of a gemstone and of determining whether it has been subjected to treatment. The method is applicable to cordierites and to beryls (emeralds, aquamarines, goeshenite, morganite, heliodor, green beryl). Specifically, it is based on detailed analysis of the impurities present in the crystal structure of the gemstone. It identifies and measures the respective proportions of the impurities, of their isotopes, if any, and indeed the proportions of such and such an isotope present in such and such a configuration within the crystal.

To analyze a gemstone 2, whether cut or uncut, the first step is to determine the exact orientation of the crystal, and in particular its c—c axis, i.e. its axis of symmetry of degree 6 in the crystal lattice, extending along the longest dimension of the lattice. For this purpose, it is possible to observe the stone 2 under a magnifying glass, under a binocular magnifier, or a microscope in order to determine the direction of the mineral tubular fluid inclusions which are usually elongate along the c—c axis. It is also possible to orient the stone 2 manually stepwise under a light beam while monitoring the response of the spectrometer that is used subsequently until an orientation is obtained for the stone which gives the spectrum that is the most intense and the most characteristic. It is also possible to seek to find the most intense signal by modifying the polarization of the infrared beam.

Once the orientation of the crystal has been determined, an electromagnetic beam 4 is applied to the stone 2, said beam being constituted mainly by an infrared component generated by a source S. This beam is directed perpendicularly to the c—c axis of the crystal. If the gemstone 2 has been cut, that will normally not have taken the orientation of the crystal into account so it is highly likely that the incident beam 4 will need to be directed in a direction that is not perpendicular to the base 6 which usually constitutes the largest facet of the gemstone. Spectrometric measurement is performed in this case in the infrared and in transmission mode. On leaving the stone, the transmitted beam 8 is picked up by the detector D of a conventional Fourier transform spectrometer. The spectrometer delivers and displays a spectrum 11, 13 that is characteristic of the absorbance of the stone 2 over wavenumber ranges that are situated in this case respectively in the range 2800 cm$^{-1}$ to 2550 cm$^{-1}$, and 2450 cm$^{-1}$ to 2250 cm$^{-1}$ in the infrared.

Figure 3:
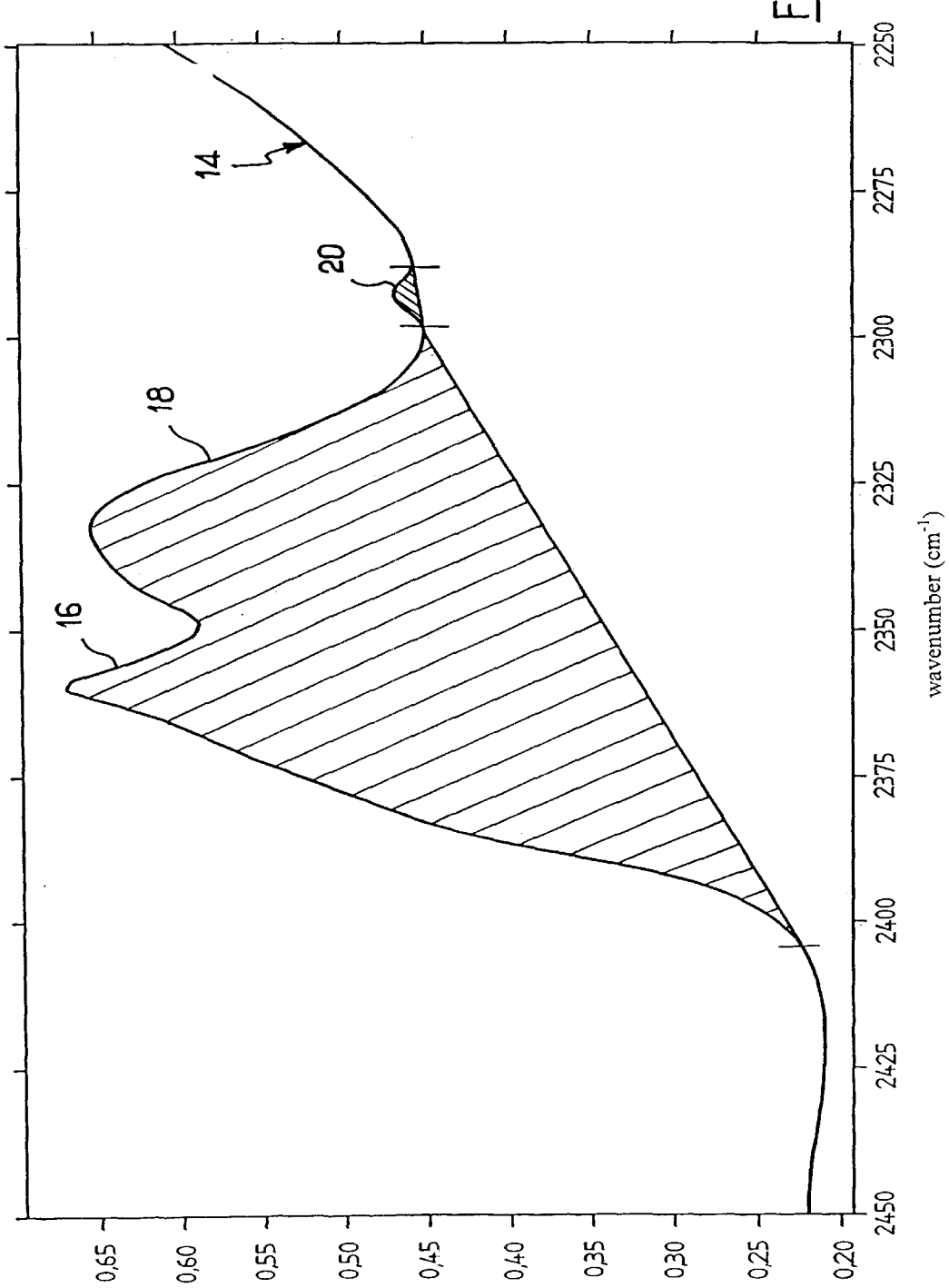

An example of these spectra 11, 13 is shown in FIGS. 2 and 3. Orienting the beam 4 perpendicularly to the axis c—c makes it possible to optimize interaction between impurities and the infrared radiation, thereby amplifying the absorbance profile of the spectra 11, 13 that are obtained, in particular for wavenumbers lying in the range 2570 cm$^{-1}$ to 2600 cm$^{-1}$.

Thereafter, initial analysis of the spectra 11 and 13 is performed on a qualitative basis, as shown in FIG. 4. This qualitative analysis seeks to determine the general profile of the absorbance spectrum within the described zone and it relates to the number, the locations, and the respective heights of the peaks that are visible in the spectra. For this purpose, a database 10 is available that contains the absorbance spectra 16, 18 over the same wavenumber range for stones of known nature and geographical origin. It is also known that the absorbance spectra of stones of the same nature or of the same origin have the same general appearance. In particular, they present peaks or bands at the same wave-numbers, i.e. located in the same positions within the spectrum. In the spectra 11 and 13, there are six such peaks and they are referenced 10, 12, 14, 16, 18, and 20.

The similarity between the spectra 11, 13 as acquired by measurement and the spectra 15, 17 known from a set of known or reference stones leads to the conclusion that the stone 2 under investigation is very close in nature to some of the reference stones. Specifically, observing the appearance of the spectra that have been obtained experimentally and comparing them with the spectra of natural emeralds coming from various countries leads to the conclusion that the stone 2 under study is almost certainly a natural emerald from Columbia. In this respect, the presence of six peaks in the following ranges respectively is characteristic: 2694 cm$^{-1}$ to 2678 cm$^{-1}$; 2676 cm$^{-1}$ to 2663 cm$^{-1}$; 2656 cm$^{-1}$ to 2620 cm$^{-1}$; 2410 cm$^{-1}$ to 2300 cm$^{-1}$; and 2300 cm$^{-1}$ to 2287 cm$^{-1}$.

For beryls, the most characteristic portions of the spectrum generally lie in the range 2570 cm$^{-1}$ to 2600 cm$^{-1}$. This qualitative first portion of the investigation enables the nature of the stone 2 to be determined and enables a certain number of potential geographical origins to be selected for the stone.

Conversely, if the stone had been treated (synthetic stone or a stone of natural origin subjected to treatment), then this qualitative analysis performed by comparison with spectra from natural stones would show that the composition of the stone is atypical, or indeed suspect, which goes some way to showing that the stone has been treated.

The second part of the investigation is quantitative, as described with reference to FIG. 5. It makes it possible to reach a final decision concerning the nature of the stone, its authenticity, and its geographical origin, and to lift most of the doubts that still persist after qualitative analysis. In practice, the nature and the authenticity of the stone 2 are identified by determining the origin thereof. In the present example, ratios are taken between suitably selected areas of the spectra 11, 13 in FIG. 2, 3 so as to normalize the absorbance magnitudes obtained and thus eliminate the effects of the dimensions of the stone 2 under investigation, and in particular the length of material through which the beam actually travels. For this purpose, areas $A_{10}$, $A_{12}$, $A_{14}$, $A_{16-18}$, and $A_{20}$ are calculated for the respective peaks (with the peaks 16 and 18 now being treated as a single peak). For this purpose, it is possible to define the surface area of the peaks as the shaded zones by drawing segments to interconnect the troughs adjacent to each peak. The five area values obtained in this case are respectively:

3.05597 u;

2.54909 u;

7.24302 u;

14.4096 u; and 1.12156 u.

These values are measured in units u that are of little importance providing only they are the same for all five values. By way of example, these units could be $cm^{-1} \times AU$ (where the ordinate is in absorbance units while the abscissa in $cm^{-1}$).

Thereafter, suitably selected ratios between these magnitudes are calculated, e.g. the ratios $r_1$, $r_2$, and $r_3$ such that:

$$r_1 = \frac{A_{10}}{A_{14}} \quad r_2 = \frac{A_{12}}{A_{14}}$$

and $$r_3 = \frac{A_{16-18}}{A_{20}}$$

In this case, these ratios give the following values:

$r_1 = 0.4219$ $r_2 = 0.3519$ $r_3 = 12.85$

Using a database 20, the values $r_1$, $r_2$, and $r_3$ are compared with corresponding ratios that are known for emeralds from each of the deposits as preselected during the qualitative step and as available in the database. In this case, the comparison shows that these values are extremely close to those of emeralds from a particular deposit X in Columbia, whereas these values are very different from the corresponding values for other deposits. It is thus extremely probable that the stone 2 under investigation is a natural emerald, that has not been treated, and that comes from deposit in Columbia. In contrast, if these ratios did not correspond to any of the ratios in the database, then the stone would have been found to be atypical in kind, and possibly suspect.

Naturally, different area ratios could be measured (e.g. $A_{10}/A_{12}$) without changing the results. The important point is to have a database 20 containing corresponding ratios for comparison purposes and to calculate those ratios which are subject to least error and which are the most revealing.

Alternatively, it is possible to measure areas that are not limited downwardly by a segment as described above, but by a segment parallel to the abscissa between ends that extend vertically down from troughs adjacent to the peak, as shown in dashed lines in FIG. 2. The segment extends to the same ordinate for two areas that are to be put into a ratio. This method amounts to increasing the areas $A_{10}$, $A_{12}$, ..., by respective bottom areas that are trapezium-shaped. Naturally, the ratios $r_1$, $r_2$ in the database need to have been calculated by the same method.

Instead of using areas, this analysis can be performed by means of the intensities associated with the peaks 10, 12, 14, 16–18, and 20. Thus, the ordinate of the top point of each peak is measured and ratios are taken between those ordinate values for comparison with known corresponding ratios. Instead of using the ordinate, it is possible to measure the relative heights of the peaks above the corresponding segment interconnecting the troughs.

The reliability of these results comes from the fact that the impurities present in the stone 2 are characteristic in terms of their respective natures and characteristics not only of the nature of the stone, but also of the geographical context of its deposit. In infrared spectroscopic analysis, these impurities generate characteristic absorption bands which are then subjected to qualitative and quantitative processing.

Specifically, the peaks 10, 12, and 14 correspond to derivatives relating to partial or total deuterization of the water molecules ($H_2O$) trapped in the gemstone, at natural dilutions. Thus, the peak 10 corresponds to the compound $D_2O$, the peak 12 probably corresponds to HDO, and the peak 14 probably corresponds to an isotope of $H_2O$. The peak 18 correspond to carbon dioxide $CO_2$, and the peak 20 to the isotope of $CO_2$ in which the carbon atom is carbon 13.

More precisely, when performing quantitative analysis, it is possible to take the ratios of internal isotopes: by taking the ratios of values (intensities or areas) that correspond to different isotopes of the same element, or to identical isotopes but in different configurations. Alternatively, or as well, it is possible to take external isotope ratios by comparing with values that correspond to unrelated species: for example the values associated respectively with deuterium and with carbon 13 dioxide. On each occasion these are local ratios, i.e. ratios performed after a particular zone of the stone has had the beam pass therethrough.

Advantageously, it is possible to perform spectral analysis over the ranges 2570 $cm^{-1}$ to 2600 $cm^{-1}$ and 2450 $cm^{-1}$ to 2250 $cm^{-1}$. The frequency range that is the richest in information often lies in the range 3200 $cm^{-1}$ to 2550 $cm^{-1}$. It can advantageously be cross checked with two other spectrum ranges lying in the ranges 2450 $cm^{-1}$ to 2200 $cm^{-1}$ and 5800 $cm^{-1}$ to 4500 $cm^{-1}$, respectively.

Advantageously, a plurality of measurements can be performed on the same stone so as to optimize quantitative diagnosis.

It is preferable to select area or intensity ratios that are the most meaningful for the spectrum under consideration and that are the most likely to quantify the measurement with the greatest accuracy and the least error associated with taking the measurements.

FIG. 6 shows preferred apparatus in accordance with the invention for implementing the method of the invention.

The apparatus 30 in this case comprises a microscope portion 32 and a detector portion 34.

The microscope portion 32 has a condenser mirror 36 used in transmission mode. It enables the electromagnetic beam to be condensed onto the center of the objective lens described below. The microscope portion also has a support plate 38 that receives the stone under investigation (not shown). It also has at least one Cassegrain type magnifying objective lens 40, and preferably has a plurality of such lenses, e.g. giving magnifications of ×15 and ×36, with the lenses being mounted on a cylinder type turret. In combination with the binocular magnifier described below, these lenses make it possible to obtain end magnifications of ×300 and ×720, respectively.

The microscope portion has a separator 42 for selecting a particular mode of illumination, either in transmission for objects that are transparent, or else in reflection, in particular for objects that are opaque or highly absorbant. In the transmission path, the beam is reflected by the mirror 36, passes through the plate 38, and through the gemstone, after which it passes through the lens 40 and the separator 42. In reflection mode, the emitted beam strikes the separator 42 directly so as to be reflected onto the gemstone. The microscope portion has rotary diaphragms 44 with a series of calibrated circular holes making it possible to select that portion of the visible or infrared beam which corresponds to the precise zone of the stone that is to be investigated. Depending on the lines that have been selected, the diameter of the beam can thus be stopped down to as little as 8 $\mu$m.

The microscope portion has a moving mirror 46 whose position serves to select the type of analysis performed on the sample. With visual analysis, dedicated to observation, the mirror reflects the beam to the binocular magnifier described below. With infrared analysis for measurement purposes, it reflects the beam to the detector 34.

Finally, the microscope portion has a binocular lens 48 for observing the stone in visible light, in association with a lens 50 that focuses the beam appropriately.

The detector portion 34 has a detector 36 and a lens 52 for focusing the infrared beam onto the sensitive element of the detector.

The microscope portion is conventional. It is manufactured and sold by Bruker Spectrospin (67166 Wissembourg, France) under the reference A590. The detector portion is manufactured by EG&G Judson (Montgomeryville, Pa. 18936, USA) and sold by the above-mentioned Bruker Spectrospin.

The detector 36 is of the MCT type (model J15D16-M205B-S 100U-45). It provides an on-axis type configuration.

This analysis technique increases quite considerably the quality of the information obtained. It makes it possible accurately to select the measurement zone (to micron scale) while making it possible to ignore the shape of the gemstone. Observation under magnification (up to ×720) is performed in visible light. The zone to be analyzed is determined by means of the series of calibrated diaphragms mounted on the rotary disk. The visible and infrared beams are accurately colinear, so only the selected portion of the stone will be analyzed (when performing the protocol described above). Under such conditions, the size of the infrared beam can be reduced to a diameter of 8 micrometers.

Using a beam this fine makes it possible to perform analysis directly on stones that are mounted while avoiding any need to remove the stones from the mounting. Measurements can be performed equally well by transmission or by specular reflection.

This technique makes it possible to reduce the observation scale and to select very precisely the proportion of the stone that is to be analyzed, in order to make the analysis easier and more reliable.

The spectrometric analysis could be implemented in diffuse reflection mode.

The beam can be oriented so as to lie in a predetermined direction that is not perpendicular to the axis c—c and that is selected as a function of the type of stone to be analyzed. However a direction perpendicular to the axis c—c generally gives the most useful results.

It is also possible to orient the beam along two or three different directions so that it is possible by vector addition to reconstitute the direction which is perpendicular to the axis c—c (with these three dimensions optionally forming an orthogonal frame of reference). A spectrum is thus obtained for each direction, and then results are combined, e.g. in linear manner, to reconstitute the spectrum which corresponds to the direction that is perpendicular to the axis c—c and that would have been obtained by direct measurements of absorption had the measurement been performed in that direction.

It is also possible to perform quantitative analysis on the basis of the OH compound.

The invention can be applied to other frequency ranges, for example in the near infrared or in the ultraviolet.

If the spectrum obtained shows saturation for a particular range of wavenumbers, a harmonic of the corresponding wavenumbers can be used to obtain a usable signal.

The stone can be analyzed in a direction perpendicular to the axis c—c without performing computations or comparing ratios and without performing any quantitative comparison.

It is possible to provide a computer 50 that includes software and that is associated with a memory that contains databases 10 and 20, the computer being capable of receiving the measurements performed by the spectrometer and of performing the above-mentioned qualitative and quantitative analyses, said computer including in particular means for performing calculations.

A method of the invention can be used in particular for detecting whether a stone is synthetic or whether a natural stone has been subjected to treatment in order to improve its authenticity artificially.

What is claimed is:

1. A method of determining an authenticity and a geographical origin of gemstones of crystal structure, the method comprising the steps of:
    applying an electromagnetic beam to a gemstone having a crystal structure;
    determining values associated with an absorbance of the gemstone for wavelengths of the beam in an absorption direction that is predetermined based on a characteristic axis of the crystal structure;
    calculating at least one ratio between said values; and
    comparing said at least one ratio with predetermined corresponding ratios belonging to gemstones of predetermined authenticity and origin.

2. A method according to claim 1, wherein the values are absorbance intensities.

3. A method according to claim 1, wherein an absorption spectrum is established corresponding to the predetermined absorption direction.

4. A method according to claim 3, wherein the values are areas defined by the absorption spectrum.

5. A method according to claim 1, wherein a beam is delivered along the predetermined absorption direction.

6. A method according to claim 1, wherein a plurality of beams are applied to the gemstone along different directions, values are determined associated with absorbance in the respective directions of the beams, and the values corresponding to the predetermined absorbance direction are calculated.

7. A method according to claim 1, wherein the predetermined direction is perpendicular to the c—c axis of the crystal.

8. A method according to claim 1, wherein at least one of the wavelengths is such that the associated value characterizes the presence of a specific body.

9. A method according to claim 1, wherein at least one of the wavelengths is such that the associated value characterizes the presence of a specific isotope of a specific body.

10. A method according to claim 1, wherein at least one of the wavelengths is such that the associated value characterizes the presence of a specific isotope of a specific body, said isotope being in a specific configuration relative to the crystal.

11. A method according to claim 1, wherein the wavelengths are situated in the infrared range.

12. A method according to claim 1, wherein the absorbance values are determined from the beam coming from the gemstone after said beam has passed through a diaphragm and/or an objective lens.

13. A method according to claim 1, wherein the gemstone is a beryl or a cordierite.

14. An apparatus for determining an authenticity and a geographical origin of gemstones of crystal structure, the apparatus comprising:
- a source of an electromagnetic beam for directing at a gemstone having a crystal structure;
- means for determining a characteristic axis of the crystal structure and thereby an absorbance direction;
- means for determining values associated with an absorbance of the gemstone for wavelengths of the beam in said absorption direction; and
- calculation means for calculating at least one ratio between the values.

15. Apparatus according to claim 14, including means for comparing the or each ratio with corresponding predetermined ratios belonging to gemstones of predetermined authenticity and origin.

16. Apparatus according to claim 14, including means for causing the beam that comes from the gemstone to pass through a diaphragm and/or an objective lens.

17. A method of determining an authenticity and a geographical origin of a gemstone of crystal structure, the method comprising the steps of:
- determining a characteristic axis of said crystal structure;
- determining an absorption direction based on said characteristic axis;
- applying an electromagnetic beam to said gemstone in said absorption direction;
- determining values associated with an absorbance of the gemstone for wavelengths of the beam in said absorption direction;
- calculating a ratio between said values; and
- comparing said ratio with predetermined corresponding ratios belonging to gemstones of known authenticity and origin.

18. The method as set forth in claim 17, wherein said characteristic axis is an axis of symmetry of degree in said crystal structure, and said absorption direction is substantially perpendicular to said characteristic axis.

* * * * *